US011925714B2

(12) United States Patent
Moughton

(10) Patent No.: US 11,925,714 B2
(45) Date of Patent: Mar. 12, 2024

(54) STERILIZING DEVICE

(71) Applicant: Strix Limited, Isle of Man (GB)

(72) Inventor: Colin Peter Moughton, Port St. Mary (GB)

(73) Assignee: STRIX LIMITED, Ronaldsway (IM)

(*) Notice: Subject to any disclaimer, the term of this patent is extended or adjusted under 35 U.S.C. 154(b) by 182 days.

(21) Appl. No.: 16/770,286

(22) PCT Filed: Dec. 6, 2018

(86) PCT No.: PCT/GB2018/053544
§ 371 (c)(1),
(2) Date: Jun. 5, 2020

(87) PCT Pub. No.: WO2019/111003
PCT Pub. Date: Jun. 13, 2019

(65) Prior Publication Data
US 2021/0145991 A1    May 20, 2021

(30) Foreign Application Priority Data

Dec. 7, 2017 (GB) ...................... 1720442

(51) Int. Cl.
*A61L 2/07* (2006.01)
*A61L 2/24* (2006.01)
(Continued)

(52) U.S. Cl.
CPC .................... *A61L 2/07* (2013.01); *A61L 2/24* (2013.01); *F26B 3/04* (2013.01); *F26B 9/003* (2013.01);
(Continued)

(58) Field of Classification Search
CPC ....................................................... A61L 2/07
See application file for complete search history.

(56) References Cited

U.S. PATENT DOCUMENTS

| 4,578,421 | A | 3/1986 | Tournier |
| 2006/0130491 | A1* | 6/2006 | Park ................ A47J 36/2433 |
| | | | 62/77 |

(Continued)

FOREIGN PATENT DOCUMENTS

| CN | 1154781 A | 7/1997 |
| CN | 2627640 Y | 7/2004 |

(Continued)

OTHER PUBLICATIONS

Translation of Taylor, 1997.*
(Continued)

*Primary Examiner* — Kevin Joyner
(74) *Attorney, Agent, or Firm* — Getz Balich LLC

(57) ABSTRACT

An apparatus for sterilizing objects includes a chamber with a heated base in thermal communication with an electric heating element; a forced air flow device arranged to direct air into the chamber; an electrical power supply circuit; a thermomechanical control in series with the electric heating element and arranged to detect a temperature of the heated base; and a thermally sensitive switch in series with the forced air flow device and arranged to detect a temperature of the heated base. The apparatus is configured to operate in a sterilization mode and in a drying mode.

23 Claims, 10 Drawing Sheets

(51) Int. Cl.
  *F26B 3/04* (2006.01)
  *F26B 9/00* (2006.01)
  *F26B 21/06* (2006.01)

(52) U.S. Cl.
  CPC ............ *F26B 21/06* (2013.01); *A61L 2202/11* (2013.01); *A61L 2202/122* (2013.01); *A61L 2202/14* (2013.01); *A61L 2202/15* (2013.01); *A61L 2202/23* (2013.01)

(56) References Cited

U.S. PATENT DOCUMENTS

2006/0218937 A1  10/2006  Park
2007/0003461 A1  1/2007   Kim
2007/0096863 A1  5/2007   Valencia Avila

FOREIGN PATENT DOCUMENTS

| CN | 201542392 U | | 8/2010 | |
|---|---|---|---|---|
| CN | 202859702 U | | 4/2013 | |
| CN | 107234078 A | * | 10/2017 | |
| CN | 206979753 U | | 2/2018 | |
| EP | 0037490 A1 | * | 10/1981 | ........... H01H 71/145 |
| GB | 2411837 A | | 4/2004 | |
| JP | S5947284 B | | 11/1984 | |
| RU | 2396091 C2 | | 8/2010 | |
| WO | 2010106348 A2 | | 9/2010 | |
| WO | 2013050011 A1 | | 4/2013 | |

OTHER PUBLICATIONS

Steris, Operating Instructions, May 27, 2005, Steris (Year: 2005).*
CN-107234078-A Translation.*
Office action for CN201880088902.1 dated Sep. 30, 2021.
JP office action for JP2020-531459 dated Dec. 15, 2022.

* cited by examiner

STERILIZING DEVICE

This application is entitled to the benefit of, and incorporates by reference essential subject matter disclosed in PCT Application No. PCT/GB2018/053544 filed on Dec. 6, 2018, which claims priority GB Patent Appln. No. 1720442.1 filed Dec. 7, 2017, which are hereby incorporated by reference in their entireties.

BACKGROUND OF THE INVENTION

1. Technical Field

The present invention is directed towards a sterilizing apparatus, particularly an apparatus for sterilizing baby bottles and their associated components.

2. Background Information

Until a baby has reached around one year old, it is regarded as necessary to sterilize all feeding equipment before each use. For example, feeding bottles, along with their associated parts including teats and covers, must be sterile before use. Sterilization prior to each use ensures that any bacteria present on the equipment is killed and therefore helps to avoid the baby becoming ill from use of the equipment.

There are various ways of sterilizing feeding equipment including: electric steam sterilizers, microwave steam sterilizers, water boilers and cold water sterilization. As will be appreciated, feeding equipment is frequently used and thus there is a need to frequently sterilize such equipment. Accordingly, a simple, easy to use sterilization apparatus is preferred by most users and many users rely upon electric steam sterilizers due to their convenience.

Electric steam sterilizers are typically stand-alone devices which may be placed on a countertop. They function by boiling water to produce steam which passes over feeding equipment contained within the device. This steam sterilizes the feeding equipment killing almost all bacteria which may be present on the equipment. Once sufficient steam has been produced, and/or the steam has passed over the feeding equipment for a sufficient amount of time to sterilize the equipment, the device is turned off and its contents are allowed to cool and dry. Typical electric steam sterilizers utilize a relatively low power heating element to heat the water to produce the steam. As a result of the use of low power elements, the sterilization process can take a considerable amount of time. Furthermore, once the sterilization process has completed, the drying and cooling of the equipment can take a long time. Due to the nature of babies and their feeding routines, a user typically will not have a long period of time in which they are free to wait for the equipment to dry and so this can be problematic.

More sophisticated electric steam sterilizing devices further include a fan which directs air into the device to help speed up the drying process. Whilst these devices offer a drying time which is reduced, when compared to the more basic device discussed above, they are, however, more expensive. The cost of these devices is not only increased due to the provision of a fan but is also increased by the associated electronic controls which control when the sterilization ends and when the fan begins.

SUMMARY OF THE INVENTION

The present invention, which aims to address or at least mitigate the above mentioned problems, provides an apparatus, for sterilizing objects, comprising: a chamber, for housing objects to be sterilized, wherein the chamber comprises a heated base in thermal communication with an electric heating element; a forced air flow device arranged to direct air into the chamber; an electrical power supply circuit arranged to supply the electric heating element and the forced air flow device with electrical power; a thermomechanical control arranged in the electrical power circuit in series with the electric heating element, and arranged within the apparatus to detect a temperature of the heated base; and a thermally sensitive switch arranged in the electrical power circuit in series with the forced air flow device and arranged within the apparatus to detect a temperature of the heated base; wherein the apparatus is arranged to operate in a sterilization mode, in which the electrical heating element is supplied with electrical power via the electrical power supply circuit, thereby heating the heated base and thus heating water, in use, within the chamber to produce steam for sterilizing the objects, and wherein the thermomechanical control is arranged to disconnect the electrical power supply to the electrical heating element, thereby ending the sterilization mode, when the thermomechanical control detects a first predetermined temperature of the heated base; and wherein the apparatus is further arranged to operate in a drying mode, in which the forced air flow device is supplied with electrical power via the electrical power supply circuit, thereby directing air into the chamber, and wherein the thermally sensitive switch is arranged to connect the electrical power supply to the forced air flow device, and thereby initiate the drying mode, when the thermally sensitive switch detects a second predetermined temperature of the heated base indicative of substantially all of the water within the chamber having been converted to steam.

The apparatus effectively operates in two modes: a sterilization mode in which steam is generated to sterilize the objects housed within the chamber and a drying mode in which air is directed into the chamber to dry the sterilized objects. Unlike prior art devices which utilize expensive, complicated, electronic controls to control their operation, the apparatus according to the present invention utilizes a thermomechanical control to control the sterilization mode and a thermally sensitive switch to control the drying mode. Advantageously these two components operate independently of one another. The provision of these relatively simple, inexpensive, components will help to reduce the cost of the apparatus and may also improve its reliability. Furthermore, the arrangement of these simple components actually allows for relatively sophisticated control of the apparatus, as will be discussed in more detail below.

It will be appreciated that the sterilization mode is characterized by the active generation of steam when the electrical heating element is energised to heat the base and boil water in the chamber. However the sterilization mode may continue beyond the point in time when substantially all of the water within the chamber has been converted to steam, i.e. the heated base has boiled dry. Sterilization may continue as long as steam is present in the chamber, even if steam is no longer being actively generated. It will further be appreciated that the drying mode is characterized by the active generation of a forced air flow when the forced air flow device is energized to direct air into the chamber. As will be apparent from the discussion below, there may be temporal overlap between the sterilization mode and the drying mode. In some embodiments the drying mode may be initiated when the sterilization mode ends. However, in various embodiments there is a temporal delay between the end of the sterilization mode and initiation of the drying mode.

The thermally sensitive switch is arranged to initiate the drying mode when it detects a second predetermined temperature of the heated base indicative of substantially all of the water within the chamber having been converted to steam. It will be appreciated that as the water is heated and converted to steam the water level within the apparatus will gradually reduce. In many embodiments the heated base will rapidly spread heat from the element, so that in practice the heated base will "boil dry" completely and start to rise in temperature. This means that the heated base may quickly have a uniform temperature and the second predetermined temperature used to indicate a "boil dry" condition may be detected from any part of the heated base. However it is envisaged that the water level may be reduced to a point at which there may still be water present in the chamber but it is not a sufficient amount to completely cover the heated base. As a result, any water remaining in contact with the heated base will likely form pools thus leaving dry portions on the surface of the heated base. As will be appreciated by those skilled in the art, the temperature of any dry portions of the heated base will increase more quickly than the portions which are still covered by some boiling water. If the thermally sensitive switch is more sensitive to the temperature of a particular region of the heated base, and if this region is dry, its temperature may rise to the second predetermined temperature even when there is a very small amount of residual water left in contact with other regions of the heated base. Accordingly, the point at which substantially of all the water has been converted to steam is also intended to cover the above described situation.

The thermomechanical control and thermally sensitive switch are each arranged to detect a temperature of the heated base. In a preferred set of embodiments the thermomechanical control and thermally sensitive switch are each arranged independently in thermal contact with the heated base. This may be direct thermal contact e.g. by being mounted directly to the heated base, or indirect thermal contact e.g. via a heat conducting medium such as heat diffuser plate.

The Applicant has recognized that there are various permutations of the temperatures at which the sterilization mode ends and the drying mode begins which would result in the desired sterilization and drying. However, in a set of embodiments, the first predetermined temperature is also indicative of substantially all of the water within the chamber having been converted to steam. Preferably, the first predetermined temperature is indicative of the temperature of the heated base at a point just as substantially all of the water is converted to steam. In other words, as soon as the thermomechanical control detects a "boil dry" condition, i.e. substantially all of the water having been converted to steam, then the thermomechanical disconnects the electrical power supply to the electric heating element and thus ends the sterilization mode. Setting the first predetermined temperature according to the above has been found to avoid excessive damage to the apparatus by preventing the apparatus from becoming too hot.

Typically, in use, the temperature of the heated base will rise to around 100° C.-105° C. (perhaps depending on exactly where the temperature is detected) at which it will remain throughout the sterilization mode whilst there is still water present in the chamber. As soon as all of the water has been converted to steam, the heated base will rapidly increase in temperature due to the lack of a medium to dissipate its heat away. The apparatus may comprise a plastics body which houses the various components of the apparatus. Accordingly, a heated base which reaches an excessively high temperature may pose a risk to the body. Therefore, by providing a thermomechanical control which disconnects the power to the electric heating element just as all of the water has been converted to steam, it prevents the heated base from becoming too hot and thus avoids damage to the apparatus. In some embodiments the first predetermined temperature is set at 125-155° C. This is the temperature detected by the thermomechanical control and of course the heated base may not have a uniform temperature distribution.

As will be appreciated by those skilled in the art, the temperature detected by the thermomechanical control may be dependent largely on how the thermomechanical control is arranged in thermal contact with the heated base. For example, if the thermomechanical control is arranged in thermal contact with a directly heated portion of the heated base, the first predetermined temperature may set to a higher temperature than if the thermomechanical control is arranged in thermal contact with a portion of the heated base spaced further from the directly heated portion, as it will be more sensitive to the temperature of the heating element and experience a higher temperature than the average temperature of the heated base. If the thermomechanical control is arranged in thermal contact with a portion of the heated base spaced further away from a directly heated portion of the heated base, it will take longer for the heat from the heating element to dissipate through the heated base towards the thermomechanical control and thus the temperature detected by the thermomechanical control will likely be considerably lower than the average temperature of the heated base. Accordingly, if arranged in this manner, the first predetermined temperature may be set lower. The degree of thermal contact between the thermomechanical control and the heated base may also affect the temperature detected at any given position. The same reasoning applies with respect to the temperature detected by the thermally sensitive switch, as will be discussed further below.

The thermomechanical control and the thermally sensitive switch may be arranged in the apparatus so as to independently detect the temperature of the same portion of the heated base. However, it may be difficult to mount the components so as to be sensitive to the exact same portion of the heated base. Therefore, in a set of embodiments, the thermomechanical control and the thermally sensitive switch are arranged to be sensitive to the temperature of different portions of the heated base. As will be appreciated, the detected temperatures of these portions may differ, e.g. depending on their respective proximity to the electric heating element, or the detected temperatures of these portions may be equivalent.

As will be appreciated by those skilled in the art, the exact detected temperatures which correspond to when substantially all of the water has been converted to steam will depend on various factors including the ambient air pressure. The first and second predetermined temperatures may be determined empirically e.g. based on likely environmental conditions.

The thermomechanical control may be arranged to keep the electrical heating element disconnected from the power supply until manually reset. The thermomechanical control may include a trip lever that is operated when the first predetermined temperature is detected. Even if this temperature is detected by a bimetallic actuator that resets when the heated base cools down, the operation of the trip lever ensures that the power supply is not re-connected until the control is reset e.g. when a user operates a manual ON switch to start the apparatus again. Such thermomechanical controls are well-known. The thermomechanical control may be one of the Applicant's U-series controls.

Due to the nature of typical electric heating elements, when the electric heating element is disconnected from the electrical power supply there will often be residual heat within the electric heating element which is able to dissipate away and further heat the heated base. As a result, typically, when the sterilization mode is ended the detected temperature of the heated base will continue to rise. The Applicant has recognized that this residual heat can be utilized in the drying mode. As the forced air flow device directs air into the chamber it will pass over the heated base, extracting heat from the base thereby heating the air within the chamber and thus accelerating the drying process. In alternative embodiments to those discussed above, in which the electric heating element is disconnected from the electrical power supply as soon as substantially all of the water has been converted to steam, the first predetermined temperature may be set at a temperature greater than a detected temperature which indicates a point at which substantially all of the water has been converted to steam. In other words, the electric heating element will remain operational for a period of time after all of the water has been converted to steam. In such embodiments the first predetermined temperature may be set at more than 155° C. This is advantageous as the heat generated by the electric heating element may be used to continue to heat the base and thus heat the air within the chamber, thereby accelerating the drying process. Of course when the electric heating element is finally disconnected from the electrical power supply in this embodiment, the heated base will similarly continue to heat the air within the chamber due to the residual heat of the heating element.

Whilst the second predetermined temperature, which is used to initiate the drying mode, is indicative of substantially all of the water having been converted to steam, it is not necessarily the temperature at which this first occurs. For example, a detected temperature of 125-155° C. for the heated base may be empirically determined to represent the point in time at which substantially all of the water has been converted to steam, however the second predetermined temperature may be set at a higher value. In embodiments where the thermally sensitive switch is arranged such that it is thermally sensitive to the same portion, or an equivalent portion, of the heated base as the thermomechanical control, the second predetermined temperature may be set at 175-195° C. or higher, preferably 190° C. for example. In these embodiments there may be a temporal delay between the end of the sterilization mode and initiation of the drying mode. It will be appreciated that if substantially all of the water is known to have been converted to steam at a detected temperature of 125-155° C., then at 175° C. substantially all of the water must have also been converted to steam. Accordingly, the second predetermined temperature is simply a detected temperature which indicates there is substantially no liquid water left within the chamber when the drying mode is initiated. However, in embodiments where the thermally sensitive switch is arranged to be sensitive to a portion of the heated base which is less directly heated by the electric heating element and thus cooler than the portion which the thermomechanical control is sensitive to, the second predetermined temperature may be adjusted to account for this lower temperature region. In a set of such embodiments, the second predetermined temperature is set at 115-140° C., preferably 130° C. for example. Therefore, whilst the actual detected temperature may be lower than the first predetermined temperature, the second predetermined temperature may be equivalent to a higher average temperature for the heated base. In these embodiments there may also be a temporal delay between the end of the sterilization mode and initiation of the drying mode.

In embodiments where the thermomechanical control and thermally sensitive switch are arranged to be sensitive to substantially the same portion of the heated base, or equivalent portions of the heated base having substantially the same temperature, then the first and second predetermined temperatures may be set at the same temperature, i.e. as the sterilization mode ends the drying mode immediately begins. However, in a preferred set of embodiments the second predetermined temperature is greater than the first predetermined temperature. In other words, the apparatus will be arranged to operate initially in a sterilizing mode, this mode will then end when it reaches the first predetermined temperature, after which there will be a short delay whilst the temperature of the heated base rises to the second predetermined temperature, before the drying mode is initiated. It will be appreciated that the first and second predetermined temperatures may be adjusted, e.g. depending on the relative thermal sensitivity of the thermomechanical control and the thermally sensitive switch, in order to achieve the above described operational sequence. Thus, in at least some embodiments, the first predetermined temperature and the second predetermined temperature are chosen such that there is temporal delay between the sterilization mode ending and the drying mode being initiated.

In some examples, the apparatus may be manually switched off, thus ending the drying mode, when a user considers that the objects are sufficiently dry. However this requires user intervention. In some examples, the drying mode may be ended by a timer. However, this introduces extra complexity to the control circuit. The applicant has devised a simple and effective way for the apparatus to automatically end the drying mode. In a set of embodiments, the thermally sensitive switch is arranged to end the drying mode by disconnecting the electrical power supply to the forced air flow device when it detects a third predetermined temperature indicative of the objects within the apparatus having dried and cooled down. In a further set of embodiments, wherein the thermally sensitive switch is sensitive to the same portion, or an equivalent portion, of the heated base as the thermomechanical control, the third predetermined temperature is set at 140-160° C., preferably 150° C. Similarly, in a further set of embodiments wherein the thermally sensitive switch is sensitive to a cooler portion of the heated base than the thermomechanical control, the third predetermined temperature is set at 80-100° C., preferably 90° C. The Applicant has recognized that when the temperature of the heated base has cooled down to this range, or preferred temperature, the objects within the apparatus should be sufficiently dry, and the temperature of the chamber is sufficiently low, that a user may extract and use the objects from the apparatus. The exact value of the third predetermined temperature may be adjusted to change the drying time.

Using the thermally sensitive switch as a means for connecting the power supply, as well as disconnecting the power supply, provides a simple, cost effective, solution for initiating and ending the drying mode. It will thus be appreciated that the apparatus is not reliant upon a timer for controlling the operational period of the drying mode. Preferably the thermally sensitive switch comprises a normally-open switch operated by a thermally sensitive actuator. The thermally sensitive actuator may operate to close the switch when it detects the second predetermined temperature (e.g. 115-140° C., in embodiments where the thermally sensitive switch is sensitive to a cooler portion of the heated base than the thermomechanical control). The thermally sensitive actuator may operate to re-open the switch when it detects the third predetermined temperature (e.g. 90° C.). The thermally sensitive actuator may be a bimetallic actuator, commonly known as a "half inch disc".

The electric heating element may be directly mounted to the heated base. However, the Applicant has recognized that it is advantageous to provide a heat diffuser plate between the electric heating element and the heated base in order to more evenly distribute heat from the electric heating element to the heated base and thus more evenly heat the water within the chamber. Therefore, in a set of embodiments, the chamber further comprises a heat diffuser plate arranged between the heated base and the electric heating element.

The electric heating element may be any suitable electric heating element, of any suitable shape, for generating and transferring heat to the heated base. However, the use of an electric heating element with an arcuate shape is particularly advantageous. Therefore, in a set of embodiments, the electric heating element is arranged in an arcuate shape and comprises electrical terminations (so-called "cold tails") defining first and second ends of the arcuate shape. Providing an electric heating element of this type is particularly advantageous as it forms a void at the center of the electric heating element into which the thermomechanical control may be mounted. Mounting the thermomechanical control in this region ensures that the control can be sensitive to the temperature of the heated base and also helps to keep the apparatus compact.

Furthermore, by providing an arcuate electric heating element there will be an indirectly heated portion of the heated base located between the cold tails. In a further set of embodiments the thermally sensitive switch is arranged to detect the temperature of the heated base between the electrical terminations. Arranging the thermally sensitive switch in this indirectly heated portion is advantageous as it is indicative of the temperature of the heated base as a whole and is less sensitive to the temperature of the electric heating element itself. As the temperature of the heated base more directly corresponds to the temperature of the water within the chamber, or indeed the lack of water within the chamber, sensing the temperature of the heated base rather than the electric heating element provides a more accurate indication of the state of the water within the chamber. As discussed previously, arranging the thermally sensitive switch so as to be sensitive to effectively, a cooler portion of the heated base, the second predetermined temperature should be adjusted accordingly such that it is still indicative of all of the water having been converted to steam. The same applies to setting of the third predetermined temperature.

The electric heating element may comprise a single element or alternatively a plurality of elements. The electric heating element may be a sheathed heating element or a thick film heating element.

The function of the thermally sensitive switch is to connect the electrical power supply to the forced air flow device after residual heat from the heating element has been distributed by the heated base into the dry chamber. The forced air flow device can then circulate the stored heat.

The forced air flow device may be arranged in any suitable position within the apparatus, for example at the base or the top of the chamber. However, in a preferred set of embodiments, the forced air flow device is arranged on a side wall of the chamber.

The forced air flow device may be arranged to redirect air already within the chamber around the chamber. However, in a preferred set of embodiments the forced air flow device is arranged to direct air from the environment in which the apparatus is placed into the chamber. Introducing, effectively 'fresh', air in this manner has been found to be advantageous as the air introduced into the chamber is less humid, i.e. has a lower moisture content, than the air within the chamber and thus helps to expel the more humid air and is more capable of taking on moisture in the apparatus thus helping to accelerate the drying process.

The forced air flow device may comprise any suitable device for forcing air into the chamber. In a set of embodiments the forced air flow device comprises an electric fan. The electric fan may be a D.C. fan, however preferably the fan is a A.C. fan as this removes the need to provide a D.C. power supply. Alternatively, the forced air flow device may comprise an air pump devoid of a fan, for example a positive displacement pump.

The forced air flow device may simply force air into the chamber thereby producing a turbulent flow of air which may be sufficient to dry the objects. However, in a set of embodiments the apparatus further comprises air directing means located downstream of the forced air flow device for directing air to specific portions of the chamber. In a further set of embodiments the air directing means is arranged to direct a first portion of air towards an upper portion of the chamber and/or a second portion of air towards a central portion of the chamber and/or a third portion of air towards a lower portion of the chamber. This Applicant has recognized that directing the air in this manner is particularly advantageous for various reasons. Directing air towards the top of the chamber helps to direct air and any steam within the chamber out of the apparatus, for example out of vents in the cover, where provided. Driving the steam out of the chamber in this manner helps to dry the contents contained therein. Further, directing air towards the lower portion of the chamber causes the air to come into contact with the heated base and to extract any heat or residual heat from the heated base, thereby cooling the heated base and heating the air, which assists in the drying process. The air directing means may be provided by any suitable structure which is capable of directing air flow. In a set of embodiments the air directing means is provided by a baffle comprising one or more vanes to direct the air flow.

In an alternative set of embodiments the air directing means comprises a conduit arranged downstream of the forced air flow device, within the chamber, to direct at least a portion of the air driven by the forced air flow device directly onto and/or into the objects housed within the chamber in use. In a further set of embodiments, the conduit directs all of the air driven by the forced air flow device. During the drying mode, it is important that the entirety of each object is completely dried to avoid the build-up of bacteria on wet parts of the objects. Accordingly, by directing at least a portion of the air into the objects within the chamber, any internal surfaces of the objects may more easily be dried.

As the primary purpose of the apparatus is to sterilize objects placed in the chamber, ensuring that the chamber remains sterile, particularly after the sterilization mode has ended, is important. As will be appreciated, there is a risk that directing air into the chamber in the drying mode will increase the risk of contaminating the sterilized objects inside the apparatus through the passing of airborne bacteria. Therefore, in a set of the embodiments the apparatus further comprises an air filter arranged to filter the air directed by the forced air flow device. The air filter may be any suitable filter, for example a high efficiency particulate air (HEPA) filter.

The air filter may be arranged upstream of the forced air flow device. However, in an advantageous set of embodiments, the air filter is arranged downstream of the forced air flow device. The Applicant has recognized that arranging the air filter downstream of the forced air flow device is advantageous for multiple reasons. For example it ensures that all of the air directed by the forced air flow device into the chamber is filtered. Further, in this downstream position, the air filter can also act as a baffle in the sterilization mode to prevent steam escaping the chamber through the forced air flow device. Preventing steam from passing back through the forced air flow device helps to ensure that the steam remains in the chamber thereby sterilizing the contents, but also it helps to prevent moisture from reaching the forced air flow device and thus avoids any moisture based damage to its electrical components. Additionally, steam which passes over the air filter will also cause the air filter to heat up which may, advantageously, sterilize the air filter itself.

As discussed previously, a quick sterilization and drying process is advantageous, particularly when the apparatus is used to sterilize feeding equipment, and therefore it is desirable for the apparatus to be capable of rapidly boiling the water within the chamber to produce steam. In a set of embodiments, the electric heating element has a power of greater than, or equal to, 2 kW, preferably 2-3 kW, and ideally about 3 kW. By providing a high power electric heating element, depending on the amount of water within the chamber, the apparatus will likely be able to rapidly boil the water and thus quickly produce steam. Furthermore, a high power element will also provide a large amount of residual heat that can be circulated in the drying mode.

The amount of water within the chamber will influence the length of time the apparatus operates in the sterilization mode as it will dictate the time it takes to heat the water to boiling and the time it then takes to convert all of the water into steam. The amount of water within the chamber must be sufficiently large that when converted to steam all of the objects are sterilized. Therefore, in a set of embodiments the chamber is arranged to accommodate 50-150 ml of water for boiling in the sterilization mode, preferably 100 ml. The Applicant has recognized that this volume of water is particularly suitable as it is a sufficient amount to convert to steam and also a sufficiently small amount that the sterilization mode is relatively short.

The heated base may take any suitable form which is capable of heating the water, in use, within the chamber. For example, the heated base may be in the form of a flat plate at the base of the chamber. However, in a preferred set of embodiments, the heated base comprises a well at its center for containing water. The well effectively forms a lowered portion in the heated base in which the water resides. The Applicant has recognized that the provision of an appropriately sized well and by filling the apparatus with enough water such that only the well, or just over the well, is filled with water, all of the water within the chamber is immediately heated when the sterilization mode is initiated, and thus the production of steam is rapid. This is contrasted to filling the apparatus with a large amount of water such that the well is filled along with a sufficient portion of the chamber, as the portion of water within the chamber, rather than the water in the well, will not be in direct contact with the heated base and will thus take longer to produce steam.

The rate of production of steam, and thus the time in which the apparatus operates in the sterilization mode, will also be at least partially dictated by the how easily the steam can escape the chamber and the pressure within the chamber. In a set of embodiments the apparatus further comprises a cover arranged to close the chamber. The provision of a cover will help to at least restrict the escape of steam from the chamber and thus increase the pressure within the chamber. This cover will therefore act to increase the rate of production of steam and thus reduce the operational time of the sterilization mode. As discussed previously, reducing the time the apparatus takes to sterilize the objects is typically preferred.

Whilst the provision of a cover helps to increase the pressure within the chamber and thus increase the rate of production of steam, it is important that the build-up of pressure is not too large as this could either damage the apparatus or cause harm to a user if hot steam is ejected from the chamber under high pressure. Therefore, in a set of embodiments the cover comprises at least one vent arranged to permit the outflow of steam from the chamber. A vent on the cover will allow some steam to escape during the sterilization mode and thus prevent the pressure from increasing to potentially dangerous levels. Furthermore, the at least one vent will also provide means for the steam and air to escape the apparatus in the drying mode, in which air is forced into the chamber.

The objects housed within the chamber may simply be placed within the chamber and rest on the heated base. However, as the heated base will typically reach high temperatures, arranging the objects in this manner may result in damage to the objects. Therefore, in a set of embodiments the apparatus further comprises a support structure for supporting objects away from the heated base. The support structure which supports the objects to be sterilized away from the heated base helps to prevent them from becoming damaged by the heated base.

The support structure may be any suitable means for supporting the objects, for example the support structure may comprise means for suspending the objects, e.g. hooks which hang from the top of the chamber. However, in a set of embodiments the support structure comprises at least one tray member arranged within the chamber to support the objects away from the heated base. In a further set of embodiments the apparatus comprises a plurality of tray members. The tray members may comprise support features to assist in the support of objects thereon. For example, the tray members may comprise a plurality of bosses, shaped and sized to support particular objects such as baby feeding bottles.

In order for the steam produced within the apparatus to pass around the chamber and over the objects being sterilized, the steam must pass through the support structure. In embodiments comprising at least one tray member, the at least one tray member preferably comprises at least one aperture arranged to permit the passage of steam therethrough. Further, in embodiments comprising at least one tray member which comprises support features, preferably the support features are provided with an aperture therethrough, or at least an aperture proximal to the support feature. For example, if the support feature comprises a boss, there may be an aperture through the boss. As will be appreciated, when an object such as a baby bottle is placed upside down on the boss, i.e. with the boss extending into the mouth of the opening of the baby bottle, the aperture will permit the passage of steam into the bottle thereby allowing the inside of the bottle to be sterilized. Alternatively, if the aperture is arranged proximal to the support feature, e.g. formed as a boss, a bottle may be placed over the boss such that the mouth of the bottle at least partially extends over the aperture as well. Similarly to the example described above, this will permit the passage of steam into the inside of the bottle.

In embodiments which comprise an air directing means comprising a conduit and at least one tray member with support features provided with an aperture therethough, or at least an aperture proximal to the support feature, preferably the conduit of the air directing means is connected directly to the aperture. Accordingly, this ensures that when an object, e.g. a bottle, is placed on the support feature, that air will be directed into the inside of the object therefore assisting in the drying process. In such a set of embodiments, preferably the conduit is connected to a portion of the aperture, e.g. half of the aperture, such that air may be driven out of the aperture via another portion of the aperture not connected to the conduit. Air which passes out of the aperture may then go on to pass over the heated base, thereby heating up, and subsequently pass around the other objects within the chamber.

As discussed previously, the heated base may continue to operate in the drying mode, or alternatively residual heat in the heated base may be utilized, to accelerate the drying process when the forced air flow device is operational. The Applicant has recognized that the drying mode may further be accelerated through the provision of an additional electric heating element. Therefore, in another set of embodiments, the apparatus further comprises an additional electric heating element arranged in the electrical supply circuit in series with the forced air flow device thereby being arranged operate in the drying mode of operation. The additional electric heating element may be arranged at any suitable position within the apparatus such that is capable of heating the air within the chamber. For example, the additional heating element may be arranged in the chamber and be exposed to the air within the chamber, e.g. an immersed heating element. Alternatively the additional heating element may be provided directly in the air flow directed by the forced air flow device, i.e. immediately downstream of the forced air flow device. Advantageously, in this arrangement all of the air directed by the forced air flow will be heated. The additional heating element may be of any suitable type, e.g. a sheathed heating element, or a coiled-wire heating element. By providing an additional heating element to heat the air within the chamber, during the drying mode the temperature of the air which is circulated around the chamber by the forced air flow device will be increased and thus due to the increased temperature any condensed water on the objects within the apparatus will dry off more quickly.

BRIEF DESCRIPTION OF THE DRAWINGS

Some preferred embodiments of the present invention will now be described, by way of example only, and with reference to the accompanying drawings, in which.

DETAILED DESCRIPTION

Figure 1:
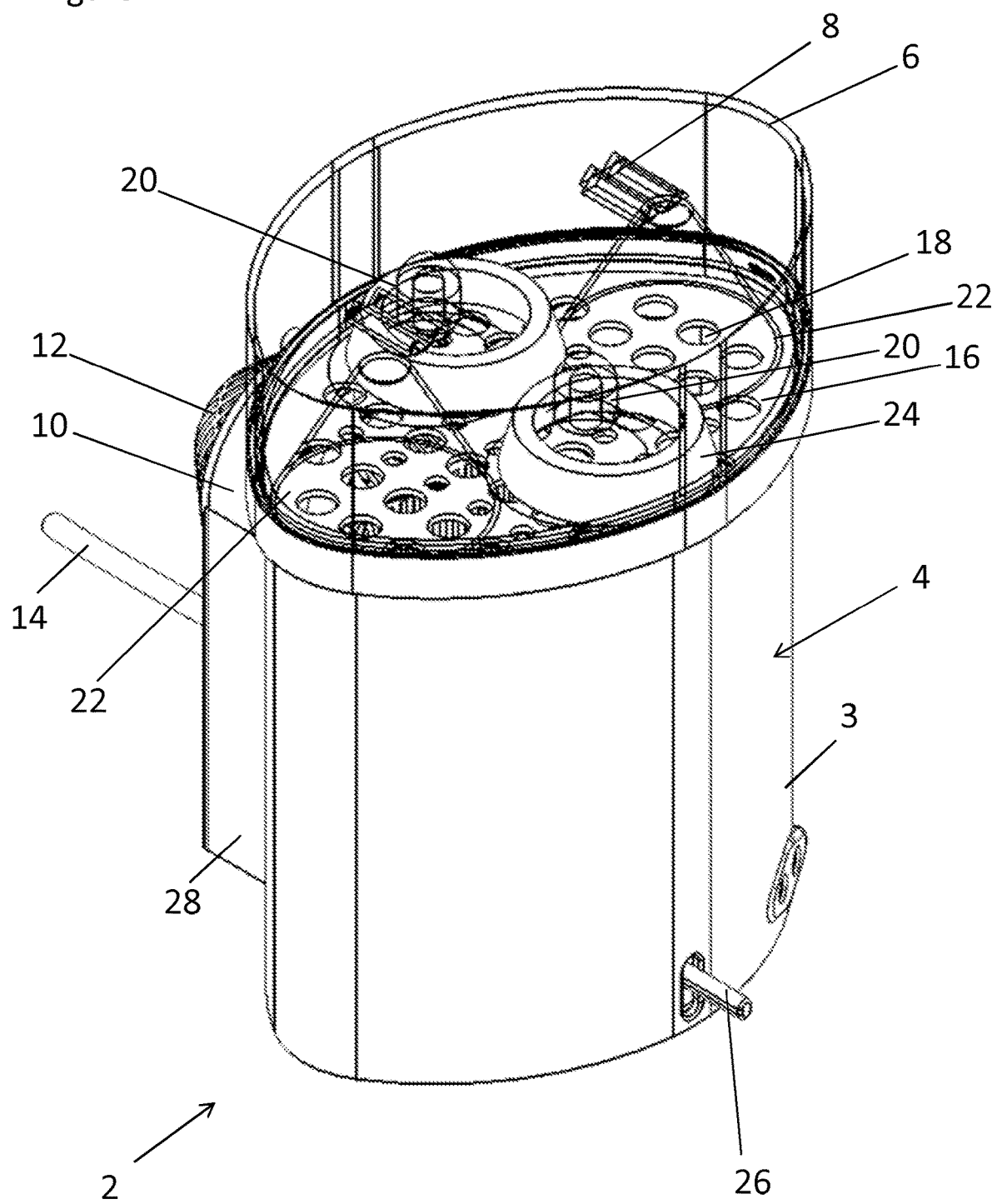
FIG. 1 shows an isometric view of an apparatus in accordance with an embodiment of the invention.

There is seen in FIG. 1 an apparatus 2 for sterilizing objects, specifically baby bottles and their associated parts. The apparatus 2 comprises an outer wall 3 which defines a main chamber 4 which is closed at its top by a cover 6. The cover 6 may be transparent or translucent to allow a user to see the objects contained within the apparatus 2. The cover 6 comprises a series of vents 8 arranged to allow steam produced within the apparatus 2 to vent. Arranged at the rear of the apparatus 2 is a forced air flow generating device in the form of an A.C. electric fan 10. The fan 10 is protected by an air intake guard 12; this component will be described in more detail later with reference to further Figures. The apparatus 2 comprises a power cord 14 which may be connected to any suitable power supply to provide power to the apparatus 2.

The apparatus 2 further comprises an upper shelf 16 arranged at the top of the chamber 4. The upper shelf 16 comprises a plurality of apertures 18 to permit the passage of steam from the chamber 4 through the upper shelf 16 into the space defined by the cover 6. In this particular embodiment, the apparatus 2 is suitable for sterilizing baby bottles and their associated parts and thus, as seen, on the top of the upper shelf 16 are a number of bottle parts including teats 20 and bottle covers 22. The cover 6 is sized so as to accommodate these parts. Also provided on the upper shelf 16 are clamp rings 24 which may be used to secure parts in place. In the embodiment shown, the clamp rings 24 are used to secure the teats 20 in position. The apparatus 2 further comprises a power switch 26 which can be used to switch the apparatus ON and OFF. Whilst the embodiment shown utilizes an AC electric fan 10, this could feasibly be replaced with a DC electric fan, for example a 12V or 24V DC fan. In such embodiments, a DC power supply (not shown) for supplying the DC fan with power may be arranged within a housing 28 at the rear of the apparatus 2. The DC power supply may be provided by an AC-DC.

In use, steam is generated in the chamber 4, as will be described in more detail later with reference to further Figures, thereby steam sterilizing any objects therein. Steam generated in the chamber 4 also passes through the apertures 18 in the upper shelf 16, thereby passing over the teats 20 and bottle covers 22 and thus sterilizing them.

Figure 2:
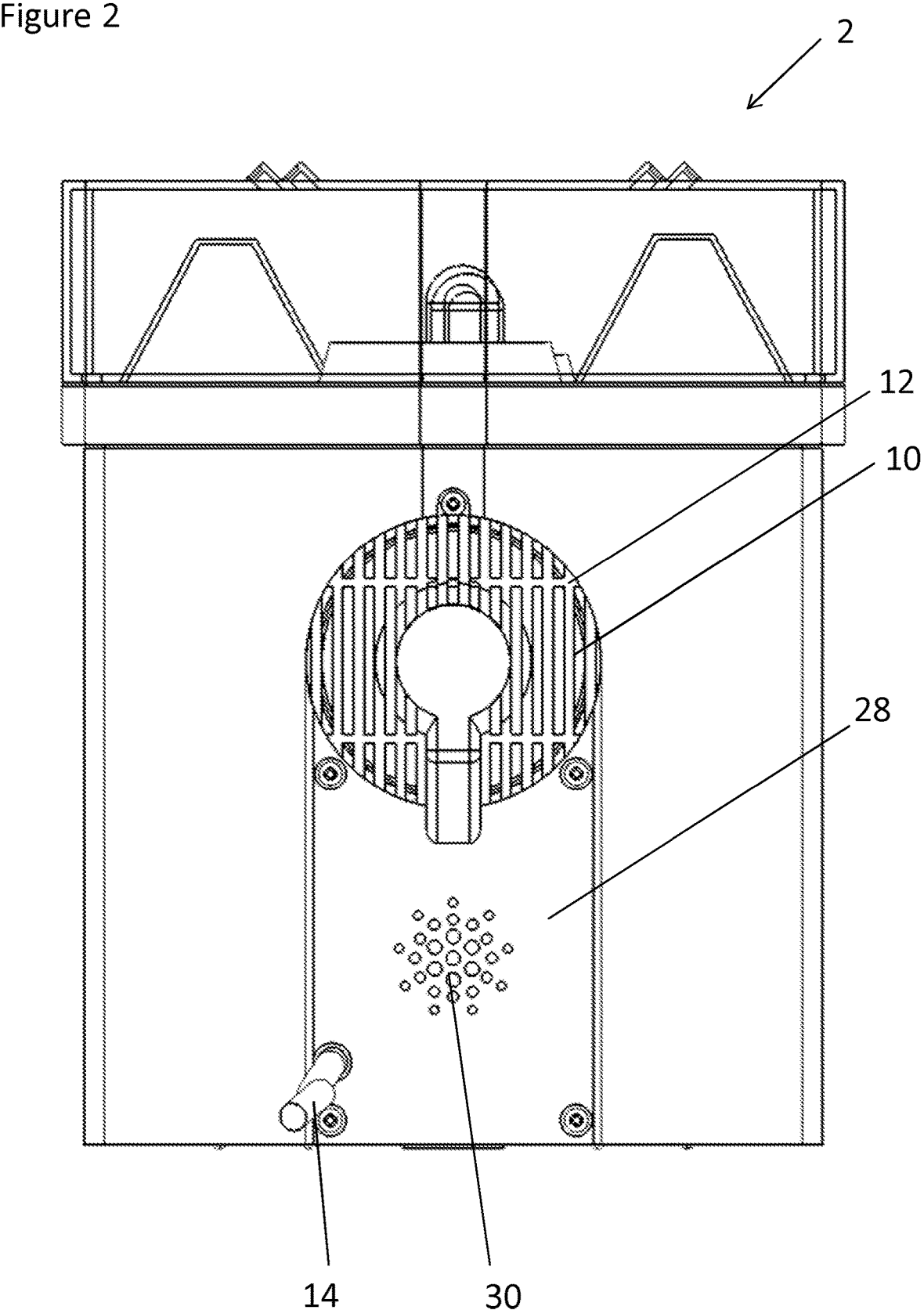
FIG. 2 shows a rear-view of the apparatus seen in FIG. 1.

FIG. 2 shows a rear view of the apparatus 2 seen in FIG. 1. It can be seen that the fan 10 and associated air intake guard 12 are mounted on the rear of the apparatus 2. The housing 28, which houses the 12 V power supply (not shown) for supplying electrical power to the fan 10, comprises a cooling vent 30 to prevent overheating of the 12 V power supply. In the embodiment shown, the vent 30 comprises a series of apertures in the housing 28.

Figure 3:
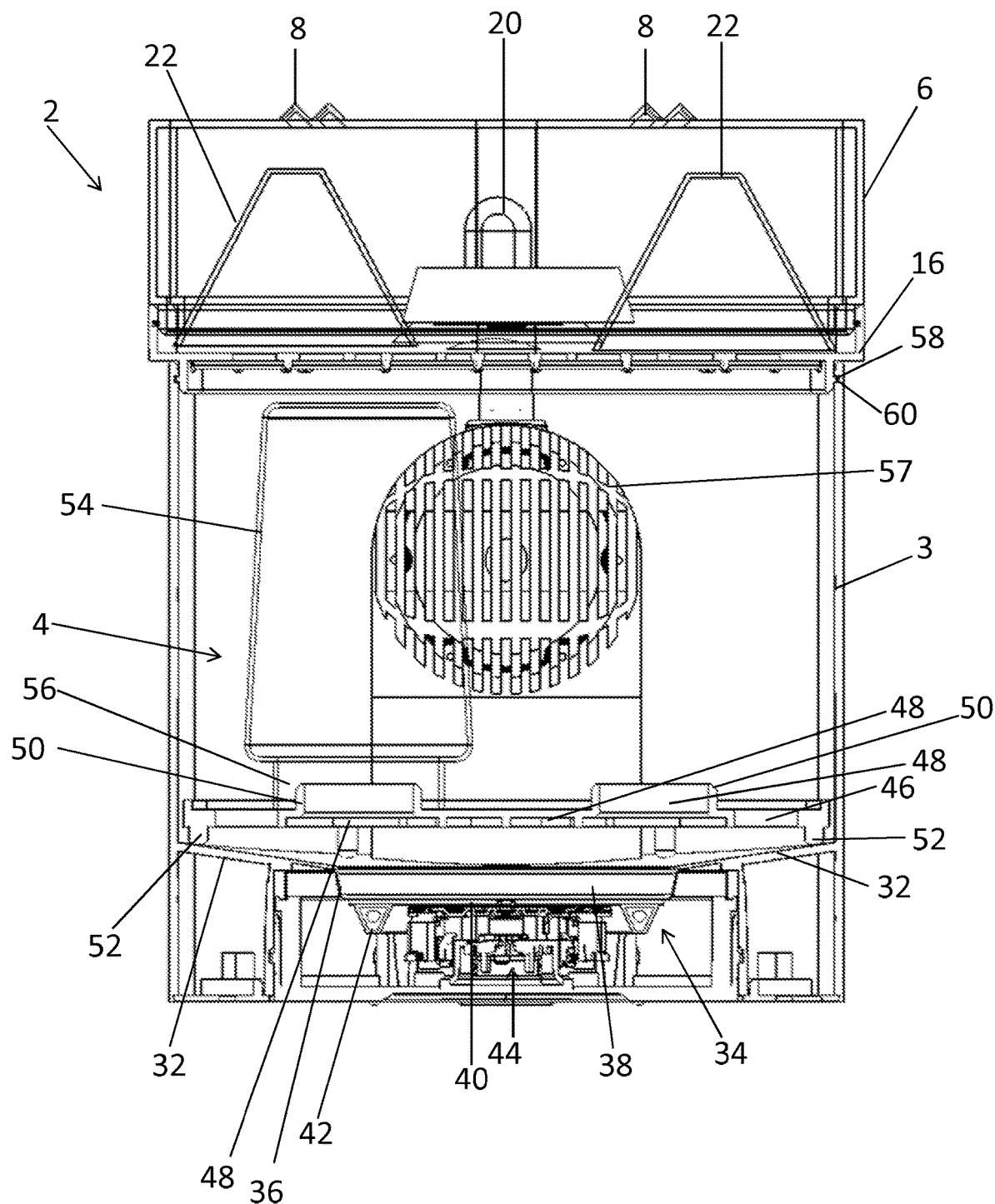
FIG. 3 shows a cross-sectional view of the apparatus seen in FIG. 1 when viewed from the front.

FIG. 3 shows a cross-sectional view of the apparatus 2 when viewed from the front. This view shows the internal components of the apparatus 2. As seen in this Figure, the chamber 4 is defined by the outer wall 3. The outer wall 3 comprises, at its lower part, an inwardly projecting annular portion 32. It will be appreciated that this inwardly projecting annular portion 32 effectively defines an aperture at its center. In the embodiment seen in FIG. 3, this aperture is closed by a heated base 34. The heated base 34 comprises a base plate 36 which is mated with the inwardly projecting annular portion 32 so as to seal the bottom of the chamber 4. The base plate 36 is formed in a dish shape and thereby forms a well 38, at the bottom of the chamber 4, in which water may reside. Mounted on the underside of the base plate 36 is a heat diffuser plate 40. Mounted below the heat diffuser plate 40 is a sheathed heating element 42. The purpose of the heat diffuser plate 40, which is sandwiched between the sheathed heating element 42 and the base plate 36, is to more evenly distribute heat across the base plate 36. As will become apparent from later Figures, the sheathed heating element 42 is arcuate in shape and thus there is a void at its center. A thermomechanical control 44 is mounted in this void and is arranged to operatively control the sheathed heating element 42.

Arranged vertically above, and spaced from, the heated base 34 is a lower shelf 46. The lower shelf 46 comprises a series of apertures 48, which can be seen more clearly in later Figures. The lower shelf 46 also comprises a plurality of bosses 50 which extend vertically upwards for supporting objects to be sterilized. The lower shelf 46 is mounted within the chamber 4 by a plurality of downwardly extending legs 52. The legs 52 rest on the inwardly projecting annular portion 32 of the outer wall 3, and support the lower shelf 46 within the chamber 4. The legs 52 have a sufficient length such that there is an air space between the heated base 34 and the lower shelf 46. As will be appreciated, by resting the lower shelf 46 within the chamber 4, rather than physically mounting it to the apparatus 2, e.g. to the outer wall 3, it may be easier for a user to remove the lower tray 46 if necessary, for example to access the space below the lower shelf 46. Whilst not visible in this Figure, the lower shelf 46 may comprise a plurality of legs 52 arranged equiangularly around the lower shelf 46. Alternatively, the lower shelf 46 may instead be provided with a continuous rim rather than discrete legs 52.

As mentioned above, the lower shelf 46 comprises a plurality of bosses 50. The bosses 50 may be used to locate an object to be sterilized on the lower shelf 46. As seen in FIG. 3, the bosses 50 may be used to locate a bottle 54 as they are shaped and sized to extend into the mouth 56 of the bottle 54. By providing a plurality of bosses 50 it may be easier for a user to locate a bottle 50 within the chamber 4. Additionally, as can be seen more clearly in later Figures, the bosses 50 each comprises an aperture 48 which extends through the lower shelf 46 thereby permitting the passage of steam therethrough. Therefore, advantageously, by placing a bottle 54 onto the boss 50, it ensures that when steam is produced by the apparatus 2, that the steam is directed into the bottle 54 via the aperture 48 located in the boss 50, thereby ensuring that the inside of the bottle 54 is sterilized. As is apparent from FIG. 3, the outer walls 3 are dimensioned such that they define a chamber 4 which is appropriately sized for containing a pair of baby bottles such as the one shown.

At the rear of the inside of the chamber 4, an air flow directing means in the form of a baffle 57 can be seen. The baffle 57 directs air from the fan 10 (not visible in this Figure), in different directions around the chamber 4. Beneath the baffle there is an air filter (also not visible) arranged to filter the air from the fan 10 before it enters the chamber 4. The air filter may be any suitable filter, for example a high efficiency particulate air (HEPA) filter.

Attached to the top of the outer wall 3 is the upper shelf 16. The upper shelf 16 comprises a peripheral flange 58 which engages with a peripheral groove 60 on the inside surface of the outer wall 3. Inherent flexibility in the material of the outer wall 3 and/or the upper shelf 16, will allow the upper shelf 16 to be easily attached and removed to/from the outer wall 3 via engagement of the flange 58 and groove 60.

Figure 4:
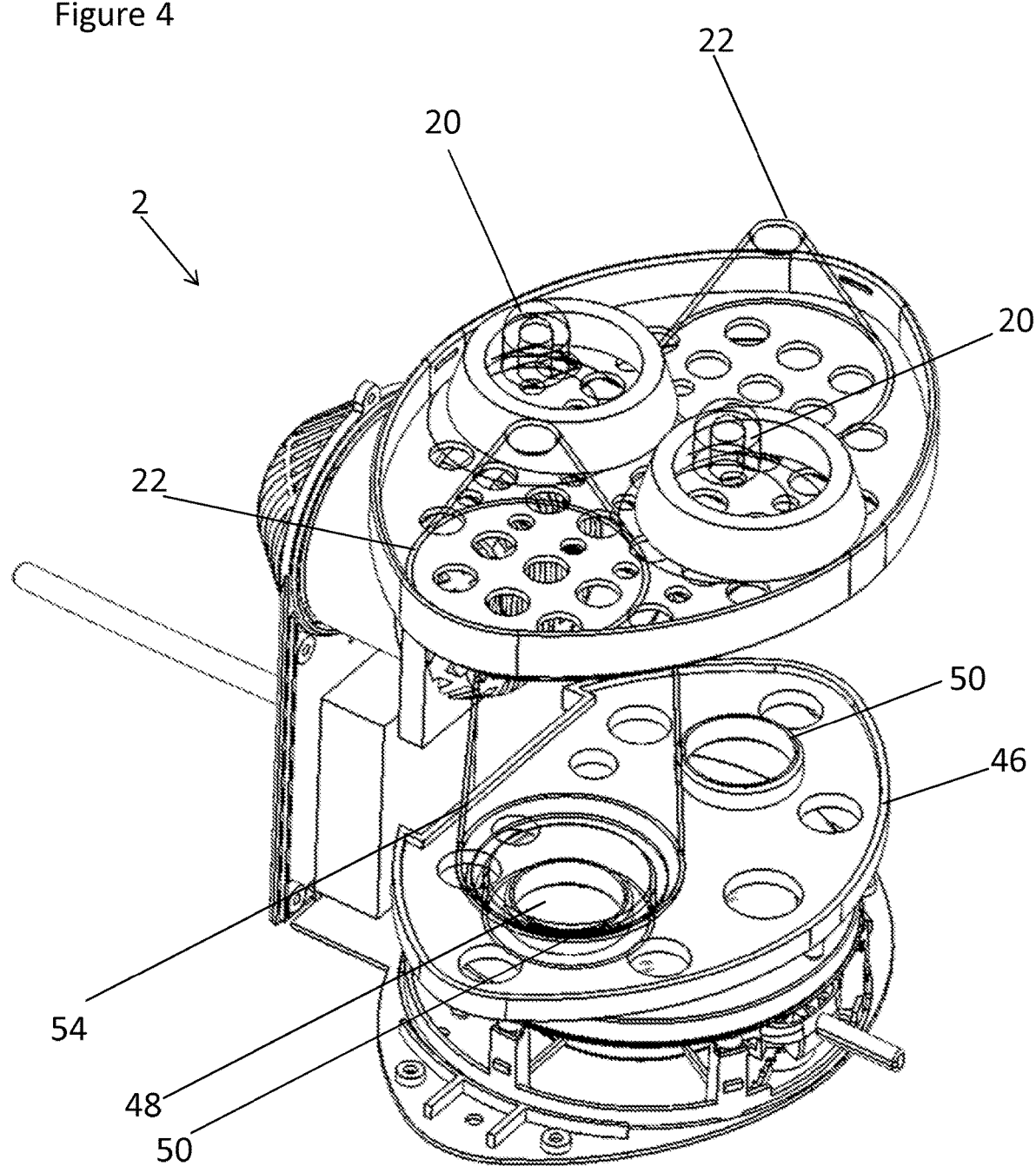
FIG. 4 shows an isometric view of the apparatus seen in FIG. 1 with the outer wall and cover removed.

FIG. 4 shows a perspective view of the apparatus 2, however the outer wall 3 and the cover 6 have been removed to more clearly show the internal components of the apparatus 2. As can be seen in this Figure, the aperture 48 located in the bosses 50 on the lower shelf 46, are such that steam which passes through the aperture 48 passes into the bottle 54. Further, the upper shelf 16 is provided with a plurality of apertures 18 which are distributed across a large portion of the surface of the upper shelf 16 such that irrespective of where the teats 20 or bottle covers 22 are placed, steam is able to pass into their inside surfaces and thereby sterilize them.

Figure 5:
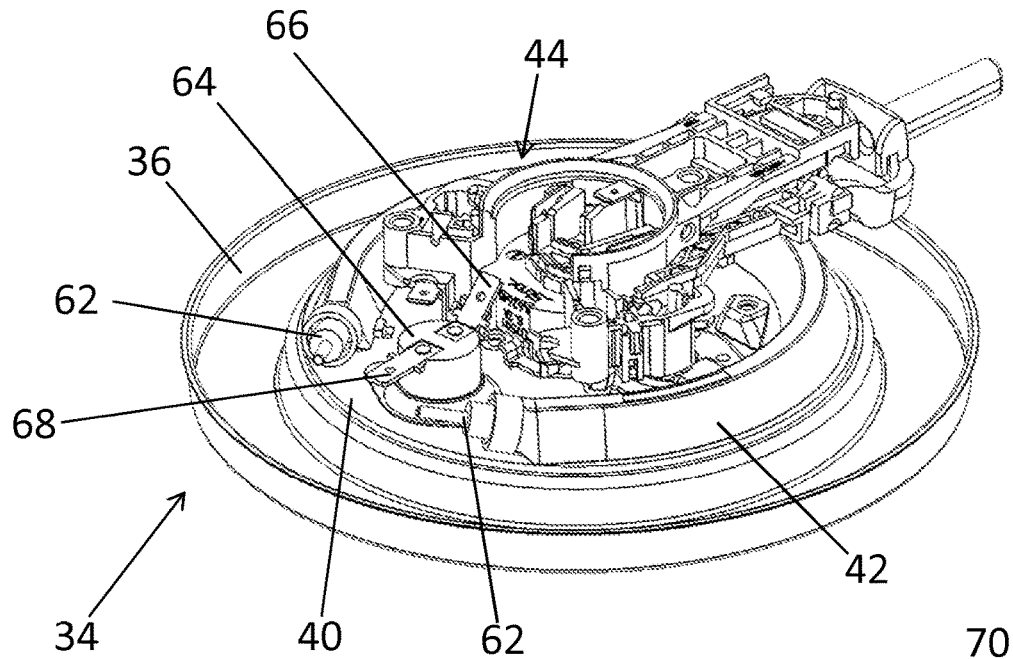
FIG. 5 shows an underside view of the heated base plate seen in FIG. 3 and FIG. 4.

FIG. 5 shows an underside view of the heated base 34 and its associated components, with the other components of the apparatus removed for clarity. As seen more clearly in this view, the heated base 34 comprises a base plate 36 to which a heat diffuser plate 40 is attached. Attached around the peripheral region of the heat diffuser plate 40 is the sheathed heating element 42 which follows an arcuate shape. The sheathed heating element 42 may be attached to the heat diffuser plate 40 via any suitable means, e.g. brazing or welding. The sheathed heating element 42 comprises a "cold tail" i.e. electrical termination 62 at either end which may be connected to a source of electrical power e.g. according to the electrical power supply circuit of FIG. 6 or otherwise.

Attached to the heat diffuser plate 40 is the thermomechanical control 44 which is arranged inside the central void defined by the arcuate sheathed heating element 42. The thermomechanical control 44 comprises a pair of bimetallic actuators (not visible in this drawing) which are arranged to be sensitive to the temperature of the heat diffuser plate 40 and hence detect the temperature of the heated base 34. The bimetallic actuators are connected to electrical switches within the thermomechanical control 44 and thus connect/disconnect electrical power to/from the sheathed heating element 42.

Also visible in this Figure is a thermally sensitive switch 64 which is attached to the heat diffuser plate 40 in the space between the cold tails 62 of the sheathed heating element 42. The thermally sensitive switch 64 may be a bimetallic actuator, such as the commonly available ½ inch disc. The thermally sensitive switch 64 comprises a first electrical terminal 66 and a second electrical terminal 68 which may be connected electrically in series with the fan 10. Accordingly, the thermally sensitive switch 64 thereby controls connection of electrical power to the fan 10.

Figure 6:
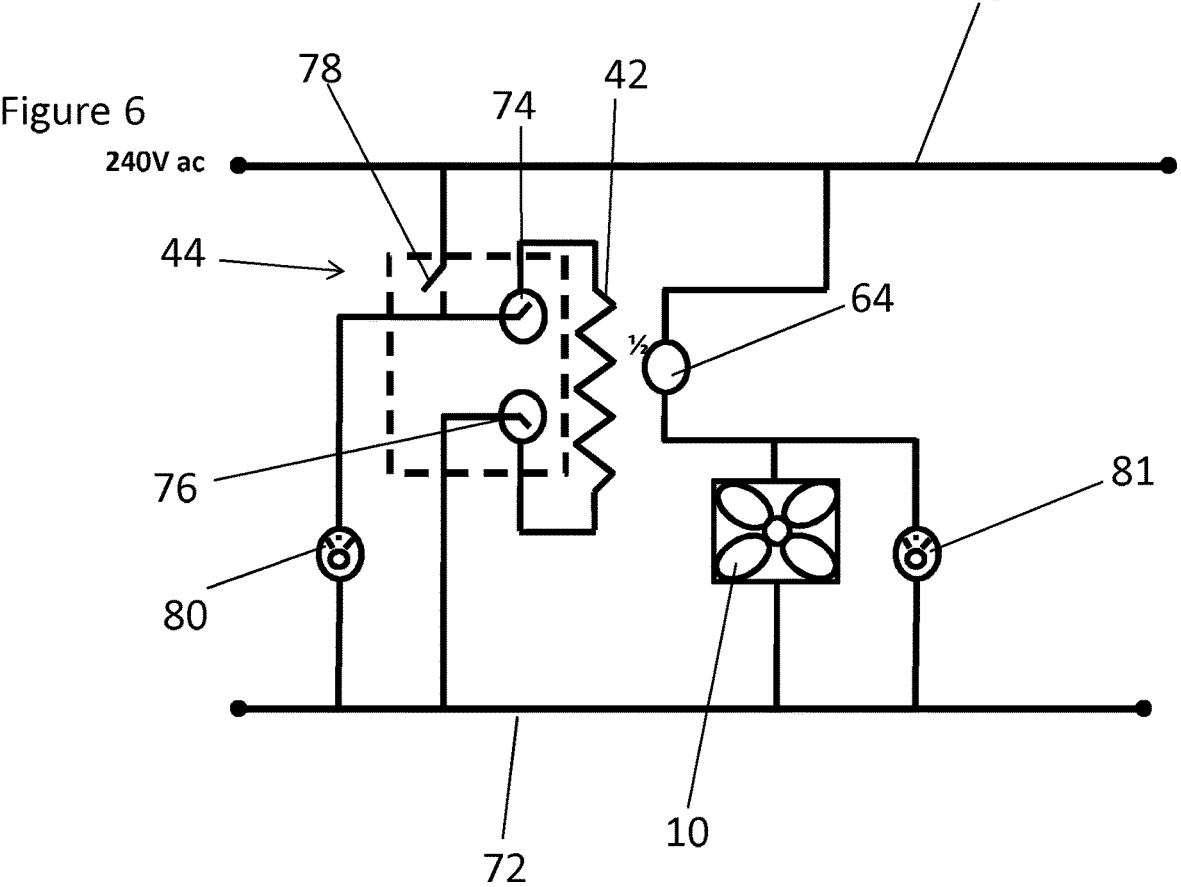
FIG. 6 shows an electrical power supply circuit for the apparatus seen in FIGS. 1-5.

FIG. 6 shows schematically an electrical power supply circuit which may be used in the apparatus 2. The electrical circuit comprises a live supply rail 70 and a neutral supply rail 72. Connected between the live and neutral supply rails 70, 72 is the sheathed heating element 42. The sheathed heating element 42 is electrically connected to the thermomechanical control 44. The thermomechanical control 44 comprises a first bimetallic switch 74 connected to one end of the sheathed heating element 42 and a second bimetallic switch 76 to the other end of the sheathed heating element 42. The thermomechanical control 44 also comprises an ON/OFF switch 78 which is also connected in series with a first light indicator 80. This may for example be an LED.

Also connected between the live and neutral supply rails 70, 72 is the electric fan 10. Connected electrically in series with the fan 10 is the thermally sensitive switch 64. Also, connected electrically in parallel with the fan 10 is a second light indicator 81.

As will be understood by those skilled in the art, when the ON/OFF switch 78 is switched to the ON position, the heating element 42 will begin to receive power and will heat up in the sterilization mode. The thermally sensitive switch 64 is normally open such that no electrical power is supplied to the fan 10 until a temperature is detected to initiate the drying mode. Operation of the electrical power supply circuit will be explained in more detail below.

Figure 7:
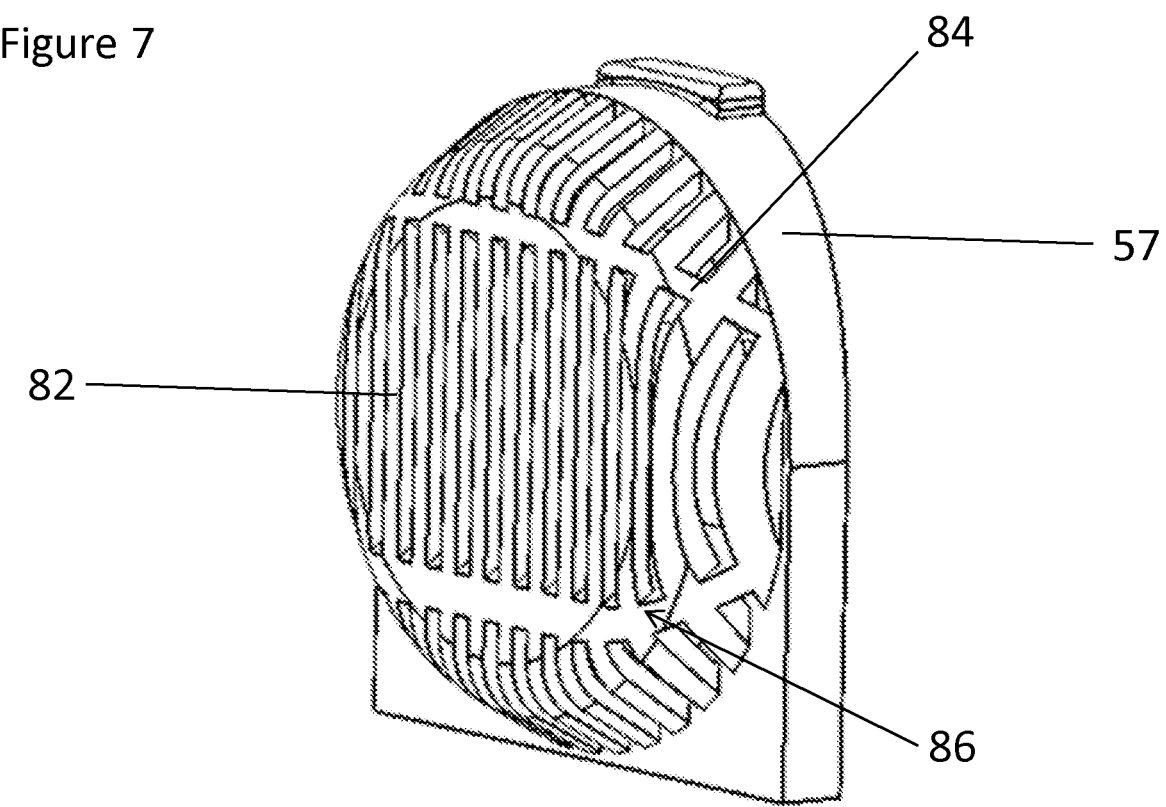
FIG. 7 shows an air flow directing means in isolation from other parts of the apparatus.
Figure 8:
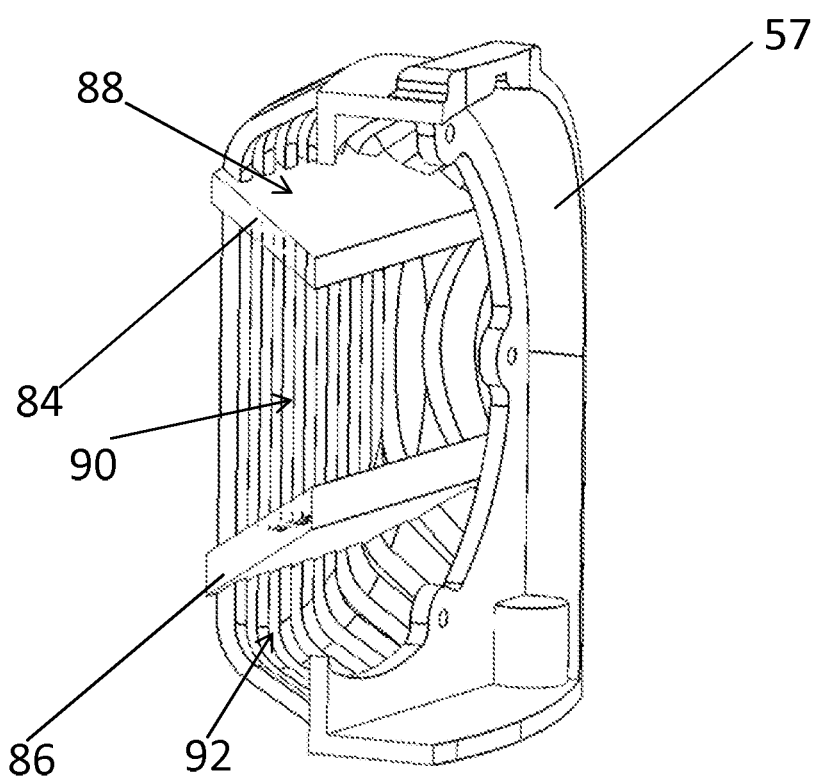
FIG. 8 shows a cross-sectional view of the air flow directing means seen in FIG. 7.

FIG. 7 shows the baffle 57 in isolation from the other components of the apparatus 2 and FIG. 8 shows a cross-sectional view, when viewed from the side, of the baffle 57. As can be seen in these Figures, the baffle 57 comprises a series of parallel vanes 82.

Air is directed by the baffle 57 by a first guide wall 84 and a second guide wall 86, which lead up to the vanes 82. The first guide wall 84 extends diagonally downwards from a top portion of the vanes 82 and the second guide wall extends diagonally upwards from a lower portion of the vanes 82. These guide walls 82, 84 effectively divide air passing through the baffle 57 into three portions: an upwards travelling portion 88, a centrally travelling portion 90 and a downwards travelling portion 92. Accordingly, when the baffle 57 is placed downstream of the fan 10, air which is forced by the fan 10 towards the baffle 57 will be divided into three portions and directed towards an upper part, central part, and lower part of the chamber 4. Directing air around the chamber 4 in this manner will assist in accelerating the drying process of the apparatus thereby allowing the bottles 54, teats 20 and cover 22 to be re-used sooner.

Figure 9:
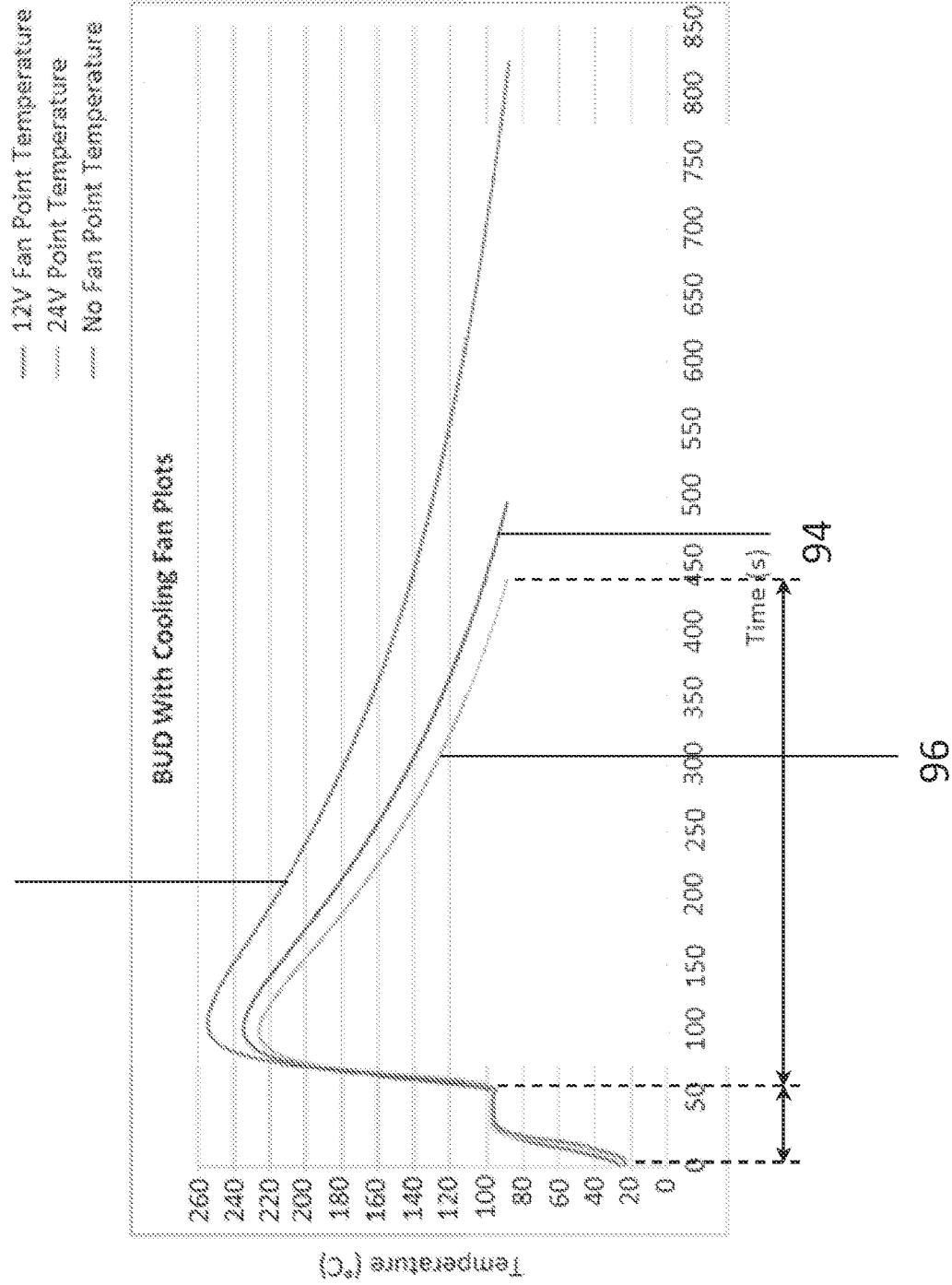
FIG. 9 shows a graph of the relative heating/sterilizing and drying times for three different apparatus.

FIG. 9 shows a graph of experimental data showing the time the apparatus 2 spends in the sterilization and drying modes. The graph shows three plots of temperature versus time. The temperature is that of the heated base 34, as measured at the location of the thermally sensitive switch 64. For each of the plots, the time period from 0 to approximately 60 seconds corresponds to the apparatus 2 operating in the sterilization mode. In this mode the temperature rises to around 100° C. at which it remains until all of the boiling water has been converted into steam. At this point, at approximately 60 seconds, all of the water is boiled off to produce steam. Once this has occurred, the temperature of the heated base 34 will rapidly increase as there is no medium to dissipate its heat. This can be seen in the plots as the sharp increase in temperature after 60 seconds. At this point, the bimetallic switches 74, 76 on the thermomechanical control 44 will quickly detect the dry boil condition (upon detecting a first predetermined temperature, e.g. 105° C.) and cut the electrical supply to the sheathed heating element 42. Whilst the sheathed heating element 42 is no longer supplied with power, the temperature of the heated base 34 will continue to rise due to residual heat within the sheathed heating element 42. Once the thermally sensitive switch 64 detects a second predetermined temperature, e.g. 120° C., it will begin operation of the fan 10. This will cause cooling within the apparatus as shown in the plots. This cooling corresponds to the drying mode.

Line 92 shows the temperature versus time of an apparatus 2 where no fan 10 is present, i.e. without a fan to assist in the drying stage. As can be seen from the plot it takes a significant amount of time for the apparatus 2 to reach a temperature below 100° C., i.e. the drying mode takes a long time. Line 94 shows temperature versus time of an apparatus where a 12 V fan is used. It can be seen that the temperature of the chamber is reduced considerably quicker when compared to the apparatus without the fan and thus the contents of the chamber 4 will be dried quicker. Line 96 shows temperature versus time for an apparatus where a 24 V is employed. It can be seen that in this apparatus the chamber is reduced to a temperature below zero quicker than the apparatus which uses a 12 V fan, thus further accelerating the drying process. The fan power therefore adjusts the cooling time.

Operation of the apparatus 2 will now be described with reference to FIGS. 1-8. When a user wishes to sterilize some baby bottles and their associated components, they must first remove the cover 6 from the apparatus 2. Once the cover has been removed, they may then remove the upper shelf 16 by disengaging the peripheral rim 58, on the upper shelf 16, and the peripheral groove 60 on the outer wall 3 of the apparatus 2. Once the upper shelf 16 has been removed, a user then has two options: they can remove the lower shelf 46 from the chamber 4 before adding water into the chamber 4, or, due to the apertures 48 on the lower shelf 46, they may simply pour water into the chamber 4 allowing it to drain through the apertures 48 onto the heated base 34.

Preferably, the chamber 4 is sized, and/or the lower shelf 46 is arranged, such that a user need only add a volume of water which does not go above the level of the lower shelf 46. This is advantageous, as when the water is boiled to produce steam, the steam can immediately pass over all of the objects within the chamber. However, this is not essential, and the chamber 4 may be filled with larger quantities of water, i.e. amounts that cause objects being sterilized within the chamber to be at least partially submerged. As will be appreciated, in this instance it will take longer for the water to boil away to a point at which steam may access some parts of the objects within the chamber 4 and thus the sterilization process may take longer. The apparatus may, for example, be provided with a device for delivering a metered quantity of water into the chamber 4, e.g. a jug. Alternatively, the chamber 4 may comprise fill markings to assist a user when filling the chamber 4 with water.

Once a user has added the required amount of water to the chamber 4 they may then insert the objects to be sterilized. In the embodiment shown, the chamber 4 is sized so as to accommodate baby bottles 54, therefore, a user may insert a baby bottle 54 by aligning the mouth 56 of each bottle 54 over one of the bosses 50. In the embodiment shown, the chamber 4 is sized so as to accommodate two bottles 54. Once the bottles 54 have been inserted, the user may then replace the upper shelf 16. Once the upper shelf 16 has been secured in position, they may then place other objects, e.g. the teats 20 and covers 22, on top of the upper shelf 16. Once the teats 20 are in position, they may be secured in position by attachment of the clamp rings 24. Finally, a user may then attach the cover 6 to close the chamber 4.

As will be appreciated, the order in which the above steps regarding filling the apparatus with water and inserting the objects to be sterilized may vary depending on the particular user or objects to be sterilized. Discussed above are two alternatives for filling the chamber 4 with water, alternatively a user may choose to first insert all of the objects to be sterilized into the apparatus 2 and then add the water. This is possible due to the apertures 18 in the upper shelf 16 and the apertures 48 in the lower shelf 46 which will permit the passage of water therethrough.

The user may then initiate the sterilization process by operating the switch 26. Once the switch 26 has been operated, e.g. by depression of the switch 26, electrical power will be provided to the sheathed heating element 42. The presence of unheated water in the chamber 4 should ensure that the bimetallic actuators 74, 76 have reset after any earlier use. The sheathed heating element 42 will therefore heat the heat diffuser plate 40 which heats the base plate 36. Any water which resides in the well 38 of the base plate 36, along with water that is in thermal contact with this water, will be heated by the base plate 36. This water will be heated to a point at which it boils and produces steam, which then leaves the surface of the water and rises through the chamber, via the apertures 48 in the lower shelf 46 in the chamber 4. This steam will pass over the bottles 54 thereby sterilizing them. Some steam will further rise into the cover 6, via the apertures 18 in the upper shelf 16, and will pass over the teats 20 and covers 20, thereby sterilizing them. Some steam may pass out of the vents 8 on the top of the cover 6. Venting of the steam in this manner avoids the build-up of pressure within the apparatus 2.

The heated base 34 will continue to heat the water within the chamber 4 until all of the water has been converted to steam. At this point, the apparatus will effectively be operating in a dry boil situation in which there is no water left to dissipate heat from the heated base 34. As a result the temperature of the heated base 34 will rapidly begin to rise. At a point at which the heated base 34 temperature reaches the first predetermined temperature, e.g. a dry boil switch off temperature, at least one of the bimetallic switches 74, 76 will operate and thereby cut the electrical power supply to the sheathed heating element 42. When this occurs, operation of one of the bimetallic switches 74, 76, will also cause the switch 78 to reset to an OFF position, thereby resetting the thermomechanical control 44. Accordingly, as will be understood by those skilled in the art, the thermomechanical 44 control resetting in this manner will avoid the heating element turning back on when the bimetallic switches 74, 76 reset.

Due to residual heat within the sheathed heating element 42, the temperature of the heated base 34 will continue to rise, as seen in the graph of FIG. 9. Once the heated base 34 reaches the second predetermined temperature, the thermally sensitive switch 64 will close, thereby switching on the fan 10. As discussed previously, the second predetermined temperature may be set to 120° C. This temperature ensures that substantially all of the water in the chamber 4 has been converted to steam, and is set higher than the first predetermined temperature so as to enable residual heat to be stored in the base 34 for use during the drying mode. The second light indicator 81 will also be illuminated. The fan 10 will thereby operate to force air into the chamber 4. The air forced by the fan 10 will be directed by the baffle 57 into all parts of the chamber 4. Air which is directed towards the lower part of the chamber 4 will impact the heated base 34 and thereby extract heat from the heated base 34. This heated air will then circulate throughout the rest of chamber 4 and assist in drying the bottles 54, teats 20 and covers 22. This will assist in the drying of any moisture which has condensed on these parts. As air is forced into the chamber 4, humid air and steam already in the chamber 4 will be forced out of the apparatus 2, via the vents 8 in the cover 6. By expelling the steam from the chamber 4 in this manner the drying process will be accelerated.

The fan 10 will continue to operate until the temperature of the heated base 34 drops to a reset temperature at which the thermally sensitive switch 64 re-opens, thereby stopping the electrical power supply to the fan 10. This reset temperature may be set, for example, at 90° C. At this point, the second light indicator 81 will also be turned off, and the drying mode will be complete. A user may then proceed to remove the cover 6 and remove the sterilized objects from within the apparatus 2 ready for use.

Figure 10:
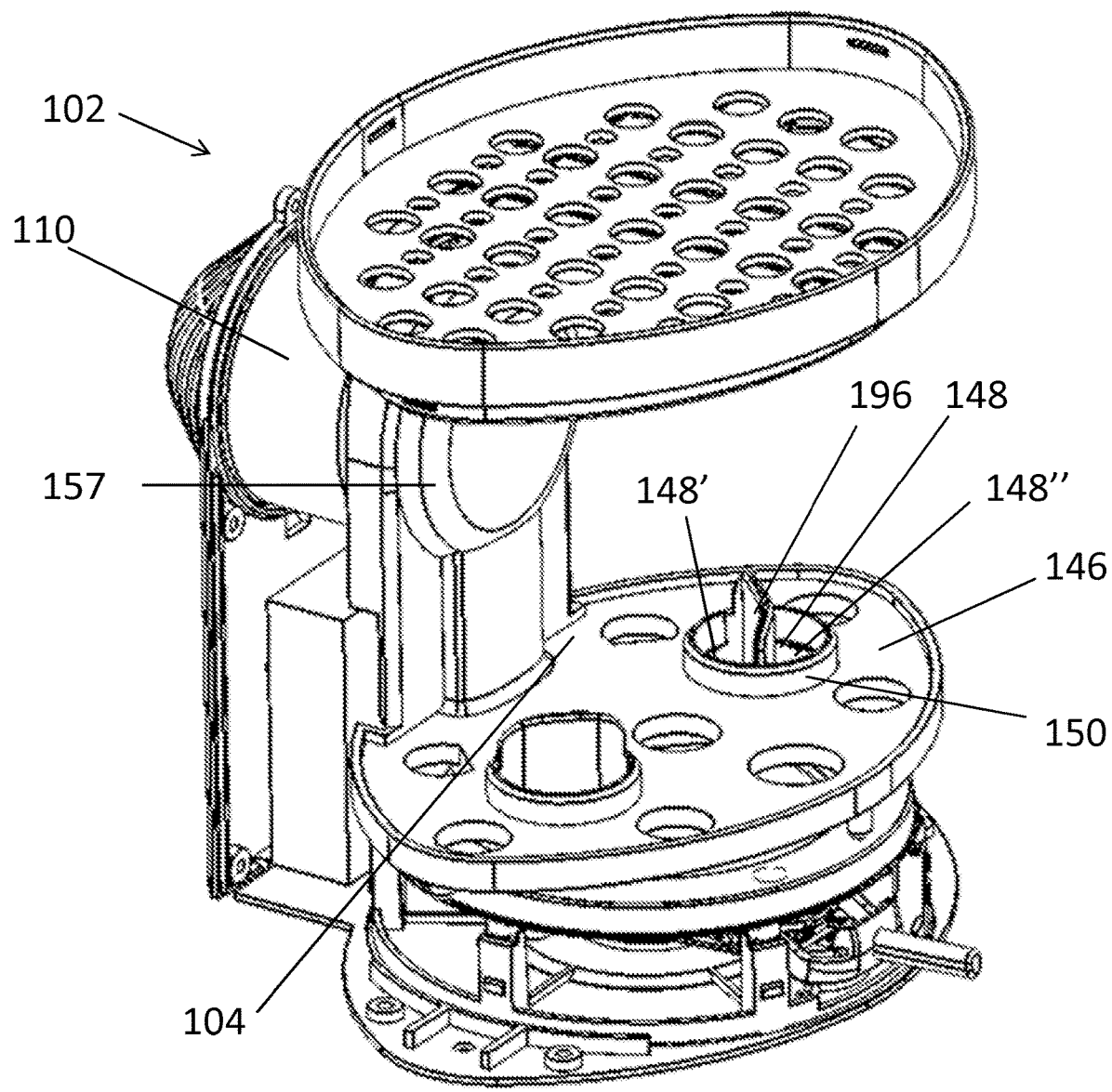
FIG. 10 shows an isometric view of an apparatus in accordance with an alternative embodiment of the present invention.

FIG. 10 shows an isometric view of an apparatus 102 according to an alternative embodiment of the present invention. For clarity purposes, the main body and cover have been removed in order to more clearly see the internal components of the apparatus 102. The apparatus 102 is essentially the same as the apparatus 2 discussed above, however instead of a baffle 57 which directs air generally into the chamber 4, this embodiment comprises an air directing means 157 which is arranged to direct air from the fan 110 along an internal conduit to apertures 148 provided in the bosses 150 on the lower shelf 146. FIG. 10 shows how the air directing means 157 comprises an upstanding guide 196 which extends through each aperture 148. The upstanding guides 196 effectively split the aperture 148 into two portions, a first portion 148' which is in fluid communication with the conduit provided by the air directing means 157, and a second portion 148" which is in fluid communication with the rest of the chamber 104. As will be understood by those skilled in the art, when a bottle (not shown) is placed over the boss 150, the upstanding guide 196 will extend into the mouth of the bottle. When air is forced by the fan 110 it will be directed by the internal conduit of the air directing means 157 directly into the bottles via the apertures 148. The air will enter the bottles via the first portion 148' of the aperture 148, pass into the bottle, and be forced out of the second portion 148" of the aperture 148, into the chamber 104. In this embodiment, air directed by the air directing means 157 to the bosses 150 will only impact the heated base after it has been expelled from the bottles.

Figure 11:
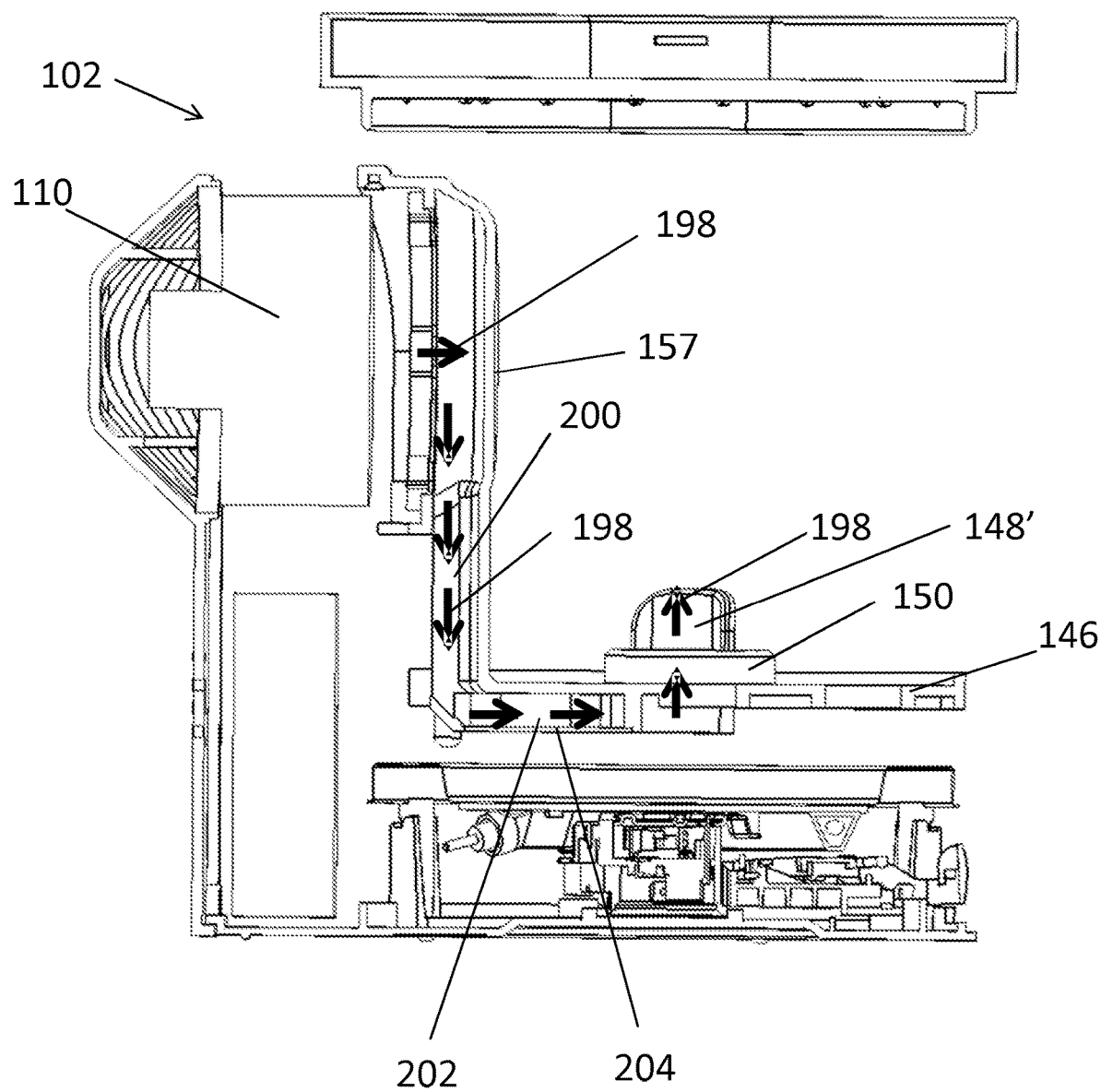
FIG. 11 shows a cross section view of the apparatus of FIG. 10 when viewed from the side.
Figure 13:
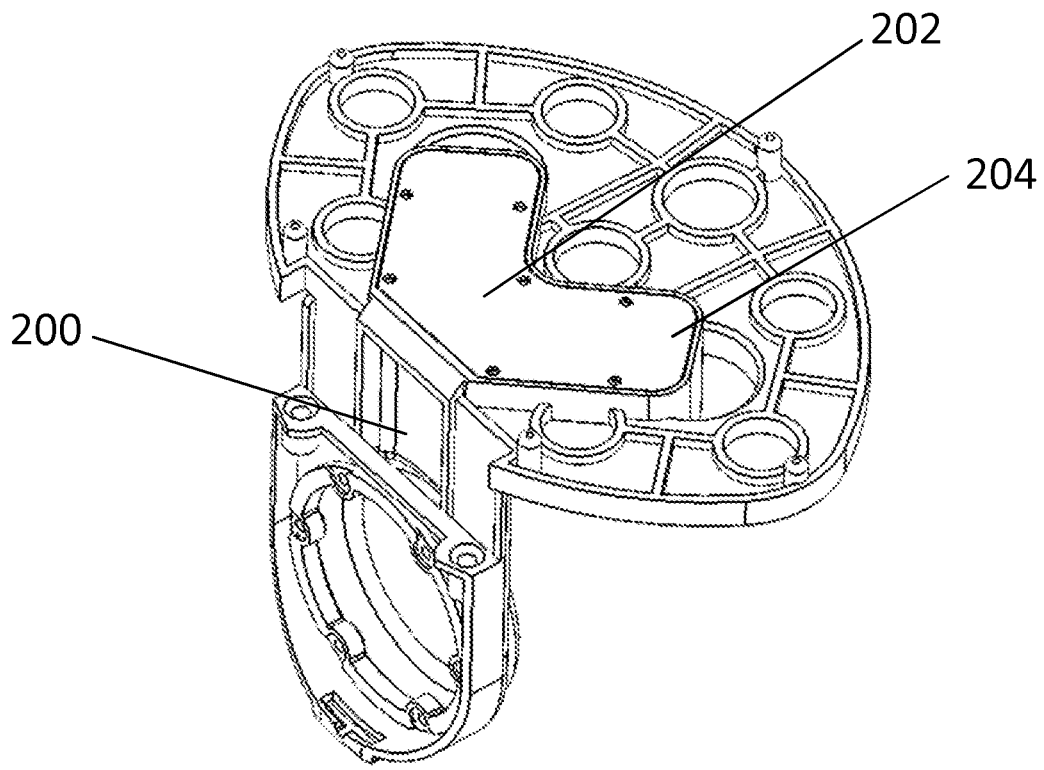
FIG. 13 shows the same underside view of the baffle and lower support tray seen in FIG. 12, with a base plate attached.

FIG. 11 shows a cross-sectional view of the apparatus 102 when viewed from the side, and more clearly shows the air flow path of the air directed along the internal conduit defined by the air directing means 157. The air flow path along the conduit is indicated by arrows 198. Air forced by the fan 110 is directed by the air directing means 157 down a conduit comprising a vertical channel 200 formed therein. Air is then directed towards the apertures 148, along a horizontal channel 202 of the conduit, which runs along the underside of the lower shelf 146. The horizontal channel 202 is closed at its base by a base plate 204, which can be seen more clearly in FIG. 13. Once the forced air has passed along this horizontal channel 202 it is then directed upwards through the first portion 148' of the aperture 148 provided in the boss 150.

Figure 12:
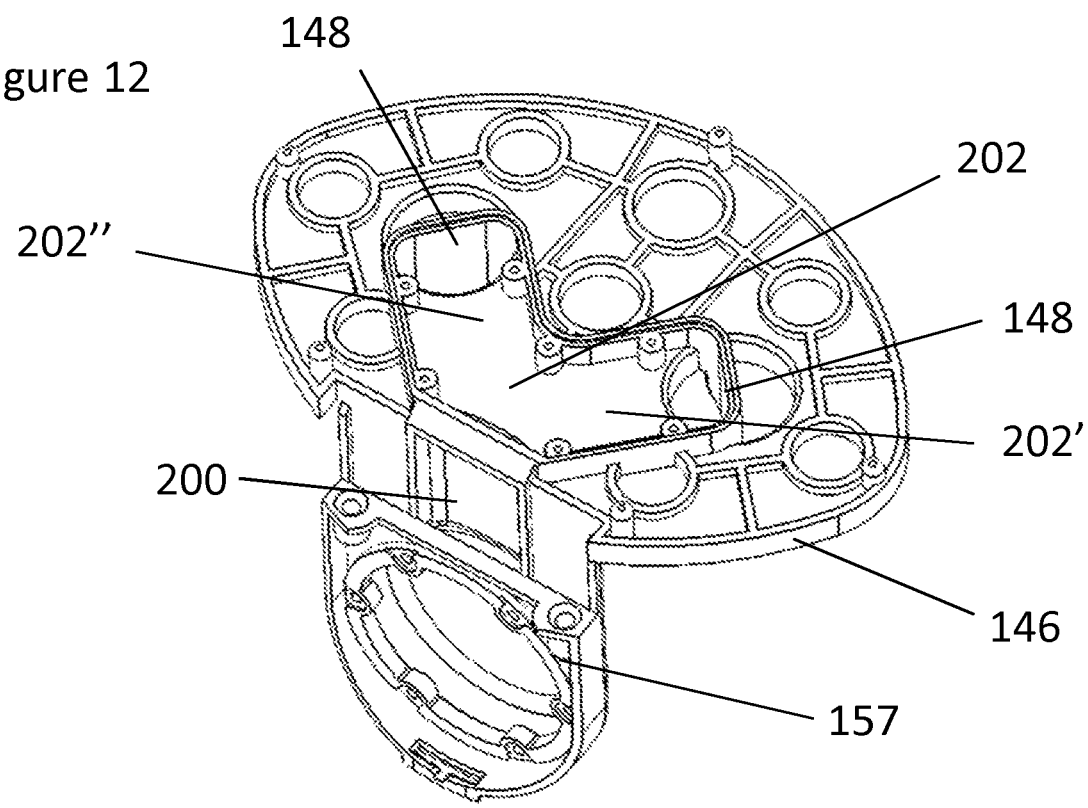
FIG. 12 shows an underside view of the baffle and lower support tray.

FIG. 12 shows an isometric view of the air directing means 157 and the lower shelf 146, when viewed from below. In this embodiment, the air directing means 157 and lower shelf 146 are formed as a single component. However, this is not essential, and the air directing means 157 and lower shelf 146 may be provided as separate components which can be attached together. As seen in this Figure, the vertical channel 200 extends into the horizontal channel 202 to form a continuous conduit. This Figure also illustrates how the horizontal channel 202 splits off into two branches, a first branch 202' and a second branch 202". Each branch 202', 202" of the horizontal channel 202 directs air to a respective aperture 148 of a respective boss 150 (on the other side).

In order to direct the air along the branches 202', 202" the horizontal channel 202 is closed at its base by a base plate 204. This can be seen in FIG. 13. The base plate 204 may be attached by any suitable means, e.g. screws. Additionally, whilst not shown in this Figure, the vertical channel 200 is closed by other components of the apparatus 102, for example the main body of the apparatus 102. Alternatively, the vertical channel 200 may also be closed by a closing plate, similar to the base plate 204.

The invention claimed is:

1. An apparatus, for sterilizing objects, comprising:
   a chamber, for housing objects to be sterilized, wherein the chamber comprises a heated base in thermal communication with an electric heating element;
   a forced air flow device arranged to direct air into the chamber;
   an electrical power supply circuit arranged to supply the electric heating element and the forced air flow device with electrical power;
   a thermomechanical control arranged in the electrical power circuit in series with the electric heating element, and arranged within the apparatus to detect a temperature of the heated base; and
   a thermally sensitive switch arranged in the electrical power circuit in series with the forced air flow device and arranged within the apparatus to detect a temperature of the heated base;
   wherein the apparatus is arranged to operate in a sterilization mode, in which the electrical heating element is supplied with electrical power via the electrical power supply circuit, thereby heating the heated base and thus heating water, in use, within the chamber to produce steam for sterilizing the objects, and wherein the thermomechanical control is arranged to disconnect the electrical power supply to the electrical heating element, thereby ending the sterilization mode, when the thermomechanical control detects a first predetermined temperature of the heated base, and then to keep the electrical heating element disconnected from the power supply until the thermomechanical control is manually reset;
   wherein the apparatus is further arranged to operate in a drying mode, in which the forced air flow device is supplied with electrical power via the electrical power supply circuit, thereby directing air into the chamber, and wherein the thermally sensitive switch is arranged to connect the electrical power supply to the forced air flow device, and thereby initiate the drying mode, when the thermally sensitive switch detects a second predetermined temperature of the heated base indicative of substantially all of the water within the chamber having been converted to steam; and
   wherein the apparatus further comprises an additional electrical heating element arranged in the electrical supply circuit in series with the forced air flow device, said additional electrical heating element thereby being arranged to operate only in the drying mode.

2. The apparatus according to claim 1, wherein the thermomechanical control and thermally sensitive switch are each arranged independently in thermal contact with the heated base.

3. The apparatus according to claim 1, wherein the first predetermined temperature is also indicative of substantially all of the water within the chamber having been converted to steam.

4. The apparatus according to claim 3, wherein the first predetermined temperature is indicative of the temperature of the heated base at a point just as all of the water is converted to steam.

5. The apparatus according to claim 1, wherein the thermomechanical control and the thermally sensitive switch are arranged to be sensitive to the temperature of different portions of the heated base.

6. The apparatus according to claim 1, wherein the first predetermined temperature is set at a temperature greater than a detected temperature which indicates a point at which all of the water has been converted to steam.

7. The apparatus according to claim 1, wherein the second predetermined temperature is greater than the first predetermined temperature.

8. The apparatus according to claim 1, wherein the first predetermined temperature and the second predetermined temperature are chosen such that there is temporal delay between the sterilization mode ending and the drying mode being initiated.

9. The apparatus according to claim 1, wherein the thermally sensitive switch is arranged to end the drying mode by disconnecting the electrical power supply to the forced air flow device when it detects a third predetermined temperature indicative of the objects within the apparatus having dried and cooled down.

10. The apparatus according to claim 1, wherein the thermally sensitive switch comprises a normally-open switch operated by a thermally sensitive actuator.

11. The apparatus according to claim 1, wherein the chamber further comprises a heat diffuser plate arranged between the heated base and the electric heating element.

12. The apparatus according to claim 1, wherein the electric heating element is arranged in an arcuate shape and comprises electrical terminations defining first and second ends of the arcuate shape, wherein the thermally sensitive switch is arranged to detect a temperature of the heated base between the electrical terminations.

13. The apparatus according to claim 1, wherein the forced air flow device is arranged on a side wall of the chamber.

14. The apparatus according to claim 1, wherein the forced air flow device is arranged to direct air from an environment in which the apparatus is placed into the chamber.

15. The apparatus according to claim 1, further comprising a baffle or a conduit located downstream of the forced air flow device for directing air to specific portions of the chamber.

16. The apparatus according to claim 15, wherein the baffle is arranged to direct a first portion of air towards an upper portion of the chamber and/or a second portion of air towards a central portion of the chamber and/or a third portion of air towards a lower portion of the chamber.

17. The apparatus according to claim 15, wherein conduit is arranged downstream of the forced air flow device, within the chamber, to direct at least a portion of the air driven by the forced air flow device directly onto and/or into the objects housed within the chamber in use.

18. The apparatus according to claim 1, wherein the heated base comprises a well at its center for containing water.

19. The apparatus according to claim 1, further comprising a cover arranged to close the chamber, wherein the cover comprises at least one vent arranged to permit the outflow of steam from the chamber.

20. The apparatus according to claim 1, further comprising a support structure for supporting objects away from the heated base.

21. The apparatus according to claim 20, wherein the support structure comprises at least one tray member arranged within the chamber to support the objects away from the heated base and wherein the at least one tray member comprises at least one aperture arranged to permit the passage of steam therethrough.

22. The apparatus according to claim 21, wherein the at least one tray member comprises at least one support feature to assist in the support of objects thereon, and wherein one or more of the support features are provided with an aperture therethrough.

23. The apparatus as claimed in claim 1, wherein the additional electrical heating element is arranged downstream of the forced air flow device.

* * * * *